(12) United States Patent
Hohlbein

(10) Patent No.: US 7,020,928 B2
(45) Date of Patent: Apr. 4, 2006

(54) TOOTHBRUSH

(75) Inventor: Douglas Hohlbein, Pennington, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 11/065,845

(22) Filed: Feb. 25, 2005

(65) Prior Publication Data

US 2005/0144748 A1 Jul. 7, 2005

Related U.S. Application Data

(63) Continuation of application No. PCT/US2003/026738, filed on Aug. 26, 2003.

(60) Provisional application No. 60/406,139, filed on Aug. 27, 2002.

(51) Int. Cl.
*A46B 9/04* (2006.01)
*A46B 7/06* (2006.01)

(52) U.S. Cl. .......................... 15/167.1; 15/201; 15/172

(58) Field of Classification Search ............... 15/167.1, 15/201, 172

See application file for complete search history.

(56) References Cited

U.S. PATENT DOCUMENTS

| | | | |
|---|---|---|---|
| 1,268,544 A | 6/1918 | Cates | |
| 2,706,825 A | 4/1955 | Blakeman | |
| 3,103,680 A | 9/1963 | Krichmar | |
| 4,488,328 A | 12/1984 | Hyman | |
| 5,355,546 A | 10/1994 | Scheier et al. | |
| 5,483,722 A | 1/1996 | Scheier et al. | |
| 5,604,951 A | 2/1997 | Shipp | |
| 5,625,916 A | 5/1997 | McDougall | |
| 5,651,158 A | 7/1997 | Halm | |
| 5,813,079 A | 9/1998 | Halm | |
| RE35,941 E | 11/1998 | Stansbury | |
| 5,839,149 A | 11/1998 | Scheier et al. | |
| 6,088,870 A | 7/2000 | Hohlbein | |
| 6,219,874 B1 | 4/2001 | Gelder et al. | |
| 6,408,476 B1 | 6/2002 | Cann | |
| 6,463,618 B1 | 10/2002 | Zimmer | |
| 6,641,764 B1 | 11/2003 | Lanvers | |
| 6,675,428 B1 | 1/2004 | Halm | |
| 2003/0084533 A1 | 5/2003 | Gelder et al. | |
| 2005/0091767 A1* | 5/2005 | Jimenez et al. | ............. 15/22.1 |

* cited by examiner

*Primary Examiner*—John Kim
*Assistant Examiner*—Laura C Cole
(74) *Attorney, Agent, or Firm*—Harris A. Wolin

(57) ABSTRACT

A toothbrush includes a head having multiple cleaning elements. One group of the cleaning elements is mounted on a movable portion of the head and another group may be fixedly mounted on the head. The movable portion of the head is attached by a flexible membrane to the fixed portion of the head so that the membrane is capable of flexing to alter its original orientation during use of the toothbrush and then recover to the original orientation randomly during use.

28 Claims, 3 Drawing Sheets

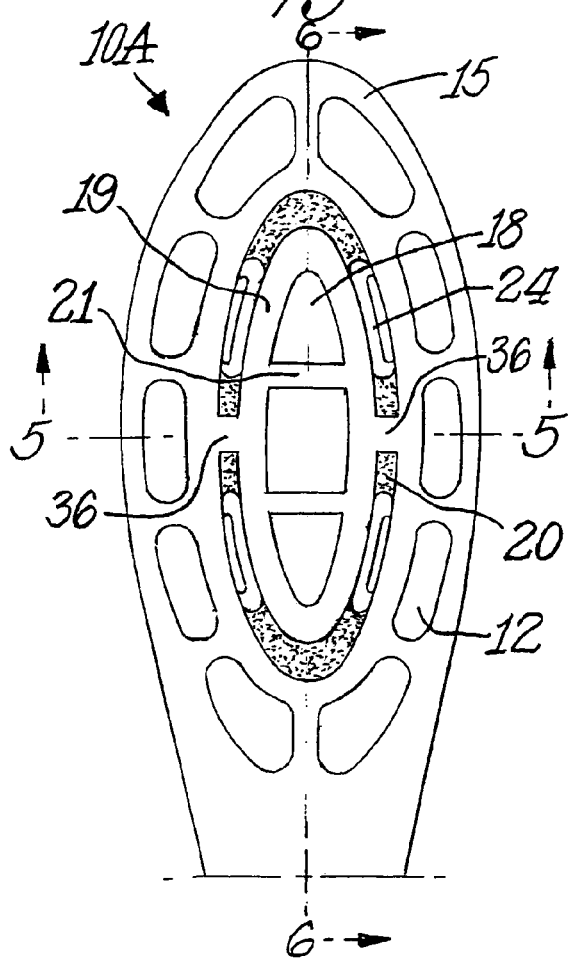
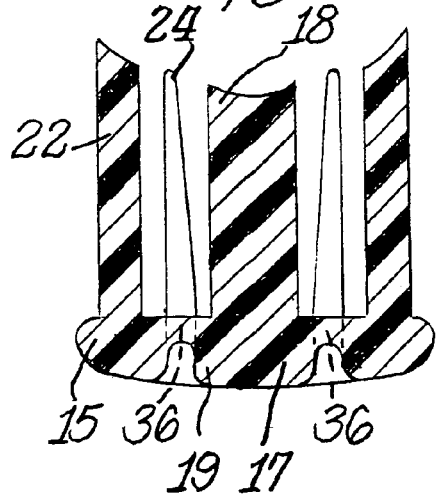
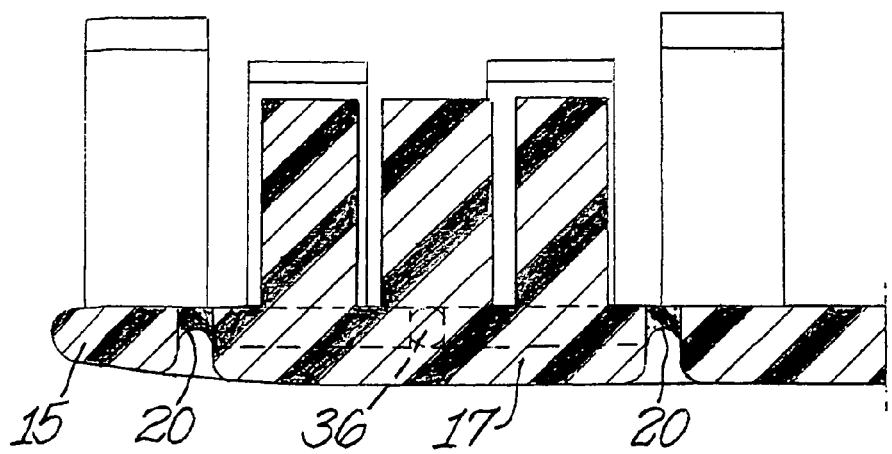

TOOTHBRUSH

CROSS-REFERENCE TO RELATED APPLICATION

This is a continuation of International Application PCT/US 2003/026738, filed Aug. 26, 2003, and claims the benefit of Provisional Application Ser. No. 60/406,139, filed Aug. 27, 2002, both of which are incorporated by reference herein in their entirety.

BACKGROUND OF THE INVENTION

The present invention is directed to a toothbrush, either manual or powered, which includes a handle and a head. Cleaning elements are mounted to the head such as tufts of bristles and/or elastomeric wipers. When toothpaste is applied to the cleaning elements the user inserts the head into the mouth and brushes the teeth in a known manner.

The head of a conventional toothbrush usually has a flat or slightly altered surface to which cleaning elements are attached. Usually the cleaning elements are strands of plastic material(s) formed into tufts, bundles or other groupings. A goal of many toothbrushes is to accommodate the cleaning element profile to that of the teeth being cleaned. Achieving that goal is complicated by the difficulty in matching a toothbrush profile to the complex surface of a typical set of human teeth. The latter generally lie in a "C" shaped curve which presents the need for a brush to address a convex outer curve and a concave inner curve. In addition, the toothbrush should be capable of cleaning irregularities on the tooth surface as well as the interproximal area between teeth.

Blakeman U.S. Pat. No. 2,706,825 issued Apr. 26, 1955 discloses a replaceable bristle head for a toothbrush. The flexible head undulates in a manner so that rows of bristles move in a direction aligned with the axis of the toothbrush handle.

U.S. Pat. Nos. 5,355,546, 5,483,722 and 5,839,149, all issued to Scheirer et al disclose cleaning elements mounted on a flexible membrane supported between a horseshoe shaped handle extension.

U.S. Pat. No. 5,651,158 issued Jul. 29, 1997 to Hans Halm discloses a toothbrush handle with a segmented head wherein adjoining segments are linked by an elastomeric material. The segments are primarily oriented transverse to the longitudinal axis of the toothbrush but may also be oriented parallel to that axis.

U.S. Pat. No. 6,088,870 discloses a latticework arrangement across the face of the toothbrush head. Tufts of cleaning elements are situated between the boundaries of the lattice and are mounted in the head so that each tuft flexes such that during brushing the bristle tufts will deflect in a manner that increases cleaning of the tooth surface.

U.S. Pat. No. 6,219,874 B1 issued Apr. 24, 2001 to Gelder, et al. discloses flexible mounting of toothbrush cleaning elements accomplished by segmenting portions of the toothbrush head, which segments are connected by flexible hinges.

U.S. Pat. No. 6,408,476 discloses another form of segmented toothbrush head with transverse grooves and an elastomeric portion joining the segments. A method of manufacturing this head is also disclosed.

SUMMARY OF THE INVENTION

This application discloses a toothbrush having multiple groupings of cleaning elements uniquely mounted to the head of a toothbrush, which mounting facilitates flexible orientation of those groupings relative to the teeth and gums being cleaned.

More particularly, the head of the subject toothbrush is designed to "wrap around" individual teeth resulting in deeper penetration of cleaning elements between teeth. This overall cleaning is accomplished by independent movement of at least two groups of cleaning elements relative to the toothbrush head and each other. The first group is a central grouping or "island" of cleaning elements flexibly mounted to the toothbrush head.

The second group is fixedly mounted to the toothbrush head in a configuration surrounding at least part of the central grouping. The central group is attached to the toothbrush head via a flexible elastomeric membrane, resilient plastic straps, webbing or other material that flexibly interconnects the first group with the toothbrush head.

In use, pressure applied to the toothbrush handle by a user causes the first group of cleaning elements to contact the teeth being cleaned. As the force applied to the toothbrush exceeds a predetermined volume, the central group of cleaning elements moves relative to the balance of the head. This movement, in turn, allows the outer group of fixed cleaning elements to contact other areas of the teeth located at a greater distance from the head, including interproximal spaces between teeth.

This desired flexibility of the central grouping of cleaning elements may be accomplished with an elastomeric bridge between the central movable group of cleaning elements and the surrounding outer group of cleaning elements. This elastomeric bridge may be continuous or may be a series of independent bridges with a void between each bridge to encourage greater flexibility. The width of this bridge can be adjusted to vary the amount of force needed to push the central group of cleaning elements into a position where the outer group can achieve their greatest cleaning potential.

In another embodiment of this invention, the gap between the groups of cleaning elements corresponding to the width of the elastomeric bridge between them can effectively be filled with elastomeric wipers that move as force is applied to the central group of cleaning elements. More particularly, tapered elastomeric wipers can be mounted to the elastomeric bridge so that the narrower tip of the wipers flex inward and outward as force is applied to and released from the toothbrush handle. This wiping action further enhances the cleaning function of the disclosed toothbrush.

THE DRAWINGS

FIG. 4 is a front elevational view of a manual toothbrush in accordance with a further embodiment of this invention;

FIG. 5 is a cross-sectional view taken along the line 5—5 of FIG. 4;

FIG. 6 is a cross-sectional view taken through FIG. 4 along the line 6—6;

DETAILED DESCRIPTION

Figure 1:
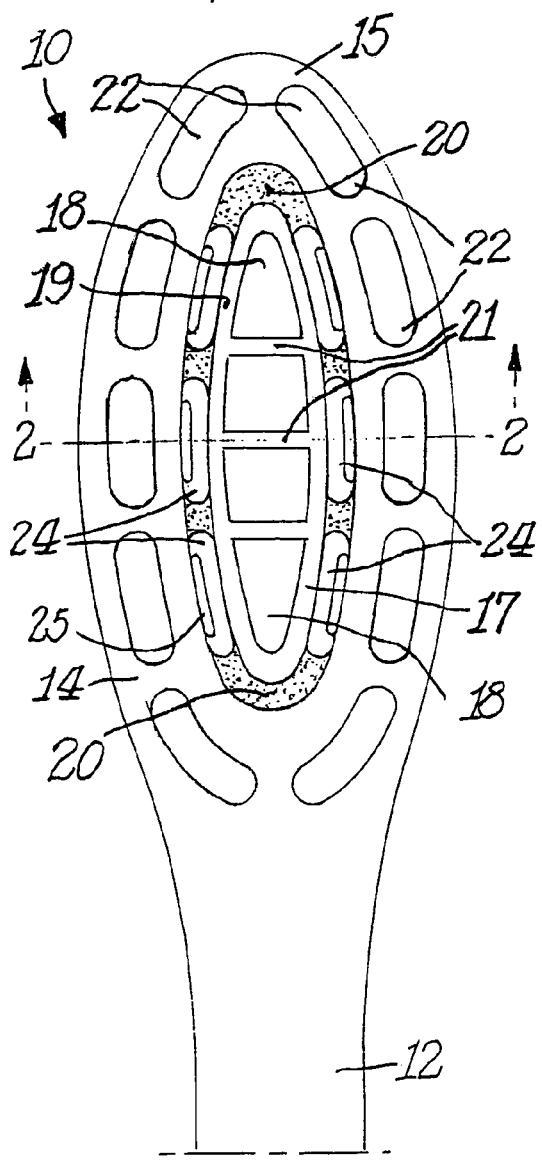
FIG. 1 is a front elevational view of a manual toothbrush in accordance with this invention.
Figure 2:
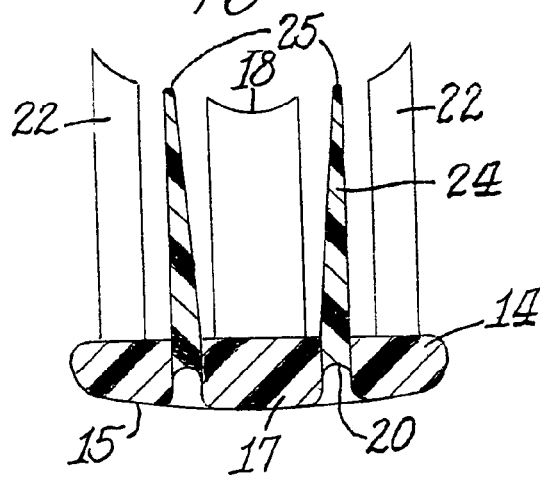
FIG. 2 is a cross-sectional view taken along the line 2—2 of FIG. 1 showing the bristle and wiper arrangement with minimal force applied to the toothbrush handle.
Figure 3:
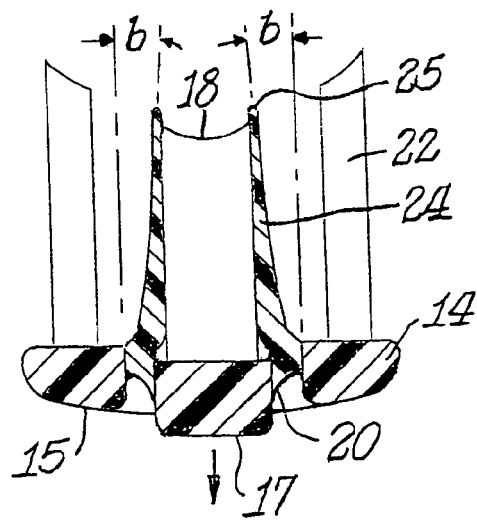
FIG. 3 is a cross-sectional view similar to FIG. 2 showing the bristle and wiper arrangement where greater force is applied to the toothbrush handle.

FIGS. 1–3 illustrate the head 14 of a manual toothbrush 10 in accordance with this invention which would be attached to a handle 12 (partially shown in FIG. 1). This invention is primarily directed to the arrangement of two groups of cleaning elements or bristles. The first group as illustrated in FIG. 1 is located in the central region of the head 14 and comprises cleaning elements 18 in the form of strands or bristles attached via anchor free tufting (AFT). Anchor free tufting is a process which generally involves mounting a plate or membrane to the toothbrush head and having the bristles or cleaning elements extend through the plate or membrane. The ends of the bristles or cleaning elements on one side of the plate or membrane would perform the cleaning function. The ends of the cleaning elements or bristles on the other side would be heated so as to be melted together and thereby be anchored in place.

The first group of cleaning elements 18 is preferably mounted on an island in a central movable portion 17 of head 14 that may be deflected downward in the direction of the arrow shown in FIG. 3 when a certain force is applied to the toothbrush handle. This movement of the central portion 17 of head 14 is facilitated by the flexible attachment of central portion 17 to the surrounding balance of the head by elastomeric or other flexible material 20 which completely surrounds island 17. The elastomeric material or membrane 20 bridges the gap between rigid hard perimeter 19 of the central movable portion 17 of head 14 and the rigid hard portion 15 of the head as illustrated in FIGS. 2 and 3.

The elastomeric material 20 should be a material or combinations of material that can flex to become altered from its original shape and recover to its original shape randomly during brushing.

As illustrated in FIG. 1 the first group of cleaning elements 18 is divided into four separate sets separated from each other by bridge members 21 which are integral and made from the same material as perimeter 19. The cleaning elements are illustrated as being relatively large elastomer walls wherein the outer elastomer cleaning elements 18 taper inwardly longitudinally toward the ends of head 14 and wherein the intermediate cleaning elements 18 have an outer surface which in combination with the outer elements form a broken coarcuate pattern separated by the bridge members. It is to be understood, however, that other forms of cleaning elements can be used including bristles and elastomeric fingers.

The first group of cleaning elements 18, flexibly mounted in head 14 are complemented by a second group of fixed cleaning elements 22 generally arrayed in a surrounding relationship with the first group 18.

FIG. 1 illustrates the second group of fixed cleaning element 22 to be in the form of generally elongated elastomer walls. Again, it is to be understood that the second group of cleaning elements 22 may also take other forms such as being elastomeric fingers or tufts of bristles.

The first and second group of cleaning elements work together as follows to provide improved cleansing of teeth.

As illustrated in FIGS. 2 and 3 when minimal force is applied to toothbrush 10 the end of the central group of cleaning elements 18 facing the toothbrush user extend approximately the same or slightly less than the distance from head 14 as the outer or fixed group of cleaning elements 22. When additional force is applied to the toothbrush, the center moveable portion 17 of head 14 slightly displaces downward (see FIG. 3). This facilitates deeper penetration of the second group of cleaning elements 22 into the interproximal areas between teeth where plaque and food deposits can cause decay.

To further promote teeth cleaning, the toothbrush 10 of this invention may include wipers 24 positioned between the two groups of cleaning elements as best illustrated in FIG. 1. These wipers are preferably made of rubber or like material with a typical cross-section such as flat, arcuate walls which taper inwardly from the surface of membrane 20 to form narrow outer ends, as illustrated in FIGS. 2 and 3. These wipers 24 extend radially from head 14 and are preferably mounted directly on the flexible elastomeric material 20 that bridges the gap between the first 18 and second groups 22 of cleaning elements. Alternatively, but less preferably, the wipers 24 could be mounted on the rigid perimeter 19. The tapered outer ends 25 of wiper 24 will move inward toward each other upon application of force to the toothbrush due to the downward displacement of the movable portion 17 of head 14. As illustrated in FIG. 3 this downward displacement of movable portion 17 of head 14 causes the outer ends 25 of wipers 24 to sweep across the teeth thereby further enhancing the cleansing action of toothbrush 10. Upon reduction of force on the toothbrush the movable portion 17 of head 14 moves back to its normal position, causing the ends 25 of wipers 24 to rotate back across the teeth. The extent of the sweeping motion of ends 25 of wipers 24 can be controlled by the location of the wipers relative to the placement of the elastomeric material 20 between the two groups of cleaning elements.

The embodiment of FIGS. 1-3 operates in a manner that when force is applied to the toothbrush head the island 17 moves generally in and out as indicated by the arrow in FIG. 3. This movement results from the soft elastomer material 20 completely surrounding island 17 thereby separating the rigid perimeter 19 of island 17 from the remaining rigid surrounding portion 15 of the toothbrush head 14. By having the wipers 24 mounted on the elastomer material or membrane 20 the in and out movement results in the wipers pivoting toward and away from the longitudinal center line of the toothbrush head as indicated by the angle "b" in FIG. 3.

FIGS. 4–7 illustrate a variation of the toothbrush 10. In the embodiment of FIGS. 4–7 the toothbrush 10A is structured so that instead of the island 17 moving in and out, the island 17 pivots along an axis transverse to the longitudinal axis of the toothbrush head in a rocking type manner. This is achieved by providing a small bridge or strap 36 connecting the center island 17 at its perimeter 19 to the outer frame 15. The strap 36 could be made of the same material such as polypropylene as the perimeter 19 and frame 15. This provides manufacturing advantages. In that regard, it is most efficient to mold both of these rigid areas 15 and 19 at the same time so that a small flow path is required to get the material from the outer frame 15 into the center island 17. The straps 36 function for the small flow paths. This connection or strap 36 could be configured to be two small round features located in the void or gap between island 17 and frame 15 on opposite sides of the island as clearly illustrated in FIG. 4. As such, the small straps 36 would act as pivot points allowing the center island 17 to rock back and forth rather than up and down as in the embodiment of FIGS. 1–3. As the head 14 rocks the wiper features 24 move together in opposite directions. In that regard, the portion of island 17 moving into the head causes the wipers to move inwards while the portion of island moving out of the head causes the wipers to move outwards.

FIGS. 4–7 illustrate the structure in operation of this variation of the invention. As shown therein island 17 includes a first group of cleaning elements 18. In this illustrated version of FIG. 4 the cleaning elements 18 are arranged in three sets rather than in four sets as in FIG. 1. Either type of arrangement could be used for the embodiments of FIGS. 1 and/or 4 as well as different types of arrangements having more or less sets of cleaning elements.

As also illustrated in FIG. 4 the island 17 includes an outer perimeter 19 with bridge members 21 separating the sets of cleaning elements. If desired, the bridge members could be omitted and the cleaning elements could be located over the entire space within the perimeter 19, as well as on the perimeter.

The elastomer 20 is also provided in the gap separating perimeter 19 from frame 15. Preferably, the elastomer extends completely around island 17 and even under straps 36 for ease of manufacture. Alternatively, the elastomer may be in the form of two U-shaped portions which extend to but not under the straps 36.

Figure 7:
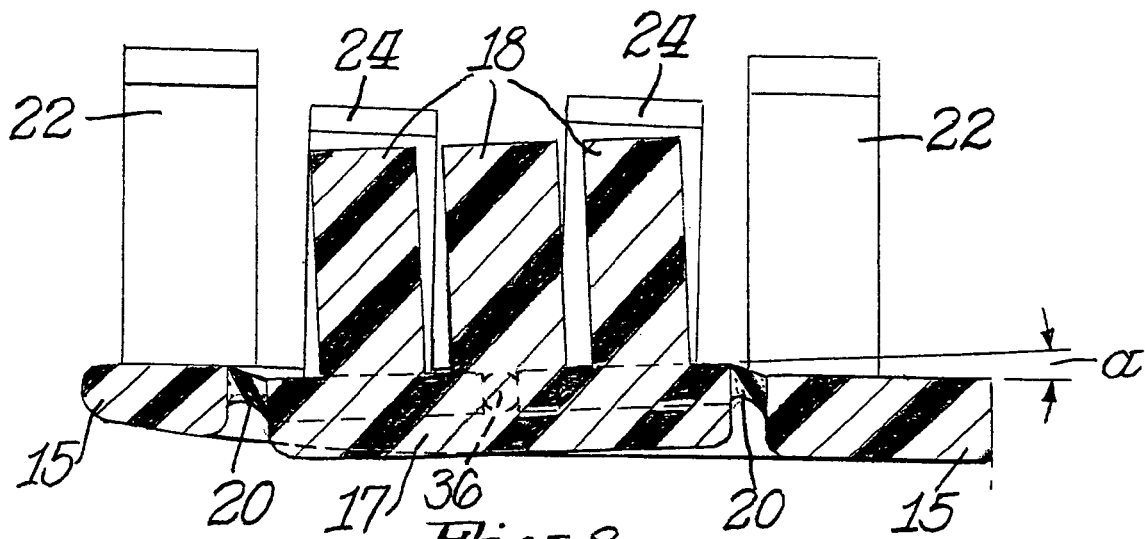
FIG. 7 is a cross-sectional view similar to FIG. 6 showing the bristle and wiper arrangement where greater force is applied to the toothbrush handle.

Again, as in the embodiment of FIGS. 1–3 the wipers 24 are mounted directly on the elastomer 20. If desired, but less preferably, the wipers could be mounted on the perimeter 19. The inclusion of the elastomer 20 is desired because its resiliency causes the island to return to its neutral position shown in FIGS. 5 and 6 when there is no longer a force applied to the toothbrush head. When, however, a force is applied the island 17 is rocked back and forth around the pivot points resulting from straps 36 as shown in FIG. 7. FIG. 7 illustrates one stage of motion where the island 17 has been pivoted to the angle "a". During this rocking motion the first group of cleaning elements 18 cooperates with the second group of cleaning elements 22 in a manner such as previously described with regard to FIG. 1-3. The wipers 24 also function their wiping action as previously described. As also previously described the elastomer 20 functions as a resilient membrane to permit the island or movable portion to flex and alter its original orientation during use of the toothbrush and to then recover to assume its original orientation randomly during use of the toothbrush and after use of the toothbrush has been completed.

Figure 8:
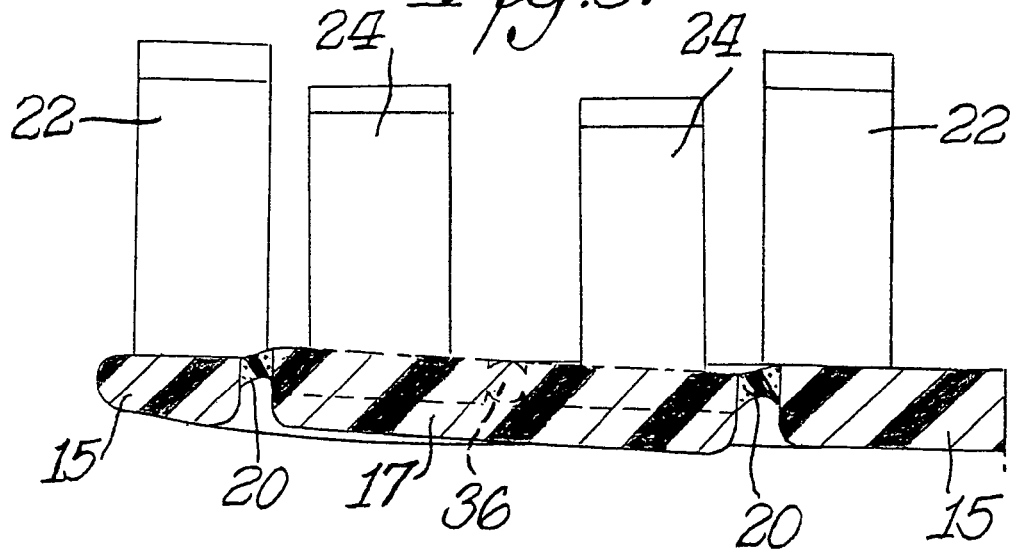
FIG. 8 is a view similar to FIG. 7 showing a different phase of operation and for the sake of clarity omitting the cleaning elements.

FIGS. 7–8 show the operation of the toothbrush when the island 17 is rocked back and forth. FIG. 8 omits the cleaning elements 18 to more clearly show the orientation of the wipers 24 during this rocking motion.

As shown in FIG. 7 when the island 17 is rocked in a counterclockwise direction the elastomeric membrane 20 on the lefthand side of strap 36 is progressively stretched in accordance with the distance away from the pivot axis of strap 36. The wipers on this downwardly stretched membrane 20 are caused to pivot in a direction toward the center of island 17 toward the pivot axis 36. On the opposite side of pivot axis 36 the elastomeric membrane 20 is stretched upwardly. The wipers 24 on the upwardly stretched membrane 20 are caused to pivot away from the pivot straps 36. Where the wipers 24 are symmetrically placed on each side of the pivot strap 36, the inclination of the wipers 24 would be parallel to each other in a direction toward the handle when rotating clockwise. If the placement of the wipers 24 is not symmetrical then the wipers which are further from the pivot axis or strap 36 would be inclined at a great angle than would be the wipers nearer to the pivot axis. FIG. 7 shows the orientation of the wipers 24 when island 17 is rocked counterclockwise at the angle "a". During this movement of the wipers 24 the cleaning elements 18 remain in a fixed orientation which in the illustrated form is perpendicular to the surface of island 17.

FIG. 8 shows the orientation of the wipers 24 when island 17 is rocked in a clockwise direction. As shown therein the wipers 24 to the right of the pivot axis or straps 36 on the upwardly stretched membrane 20 would pivot toward the center or toward the pivot axis of straps 36, while the wipers 24 on the opposite side would pivot away from the center as clearly illustrated. Thus, the result is a simultaneously opening and closing motion of the wipers during the clockwise and counterclockwise rocking motion of center island 17.

As illustrated in FIGS. 1 and 4 the island 17 is located generally along the longitudinal axis of the toothbrush head. The island 17 is generally oval shaped centrally located within the open area of the generally oval shaped frame 15.

As previously described, in the embodiment of FIGS. 1–3 the movement of island 17 is in and out in a direction generally perpendicular to the frame 15, while in the embodiment of FIGS. 4–7 the movement is a rocking movement about an axis transverse to the longitudinal axis of frame 15.

Any suitable form of cleaning elements may be used as the cleaning elements 18 and 22 in the broad practice of this invention. The term "cleaning elements" is intended to be used in a generic sense which could include conventional fiber bristles or massage elements or other forms of cleaning elements such as elastomeric fingers or walls arranged in a circular cross-sectional shape or any type of desired shape including straight portions or sinusoidal portions.

The cleaning elements, and particularly cleaning elements 18 might include one or more prophylaxis polishing cups or prophy cups which are typically made of a soft elastomeric material and are cup shaped by having a continuous or an interrupted upstanding wall forming the cup. The inner surface of the cup can contain ridges which help to clean teeth when the toothbrush is pressed against the user's teeth. More importantly, the cup shape of the prophy cups acts to hold toothpaste in place while the toothbrush is in use.

It is to be understood that the specific illustration of the cleaning elements is merely for exemplary purposes. The invention can be practiced with various combinations of the same or different cleaning element configurations (such as AFT, etc.) and/or with the same bristle or cleaning element materials (such as nylon bristles, spiral bristles, rubber bristles, prophy cups, etc.) Similarly, while the Figures illustrate the cleaning elements to be generally perpendicular to head 14, some or all of the cleaning elements may be angled at various angles with respect to the outer surface of head 14. It is thereby possible to select the combination of cleaning element configurations, materials and orientations to achieve specific intended results to deliver additional oral health benefits, like enhanced cleaning, tooth polishing, tooth whitening and/or massaging of the gums.

This invention may also be practiced where the head 14 includes one or more power or electrically operated movable sections carrying cleaning elements.

Figure 9:
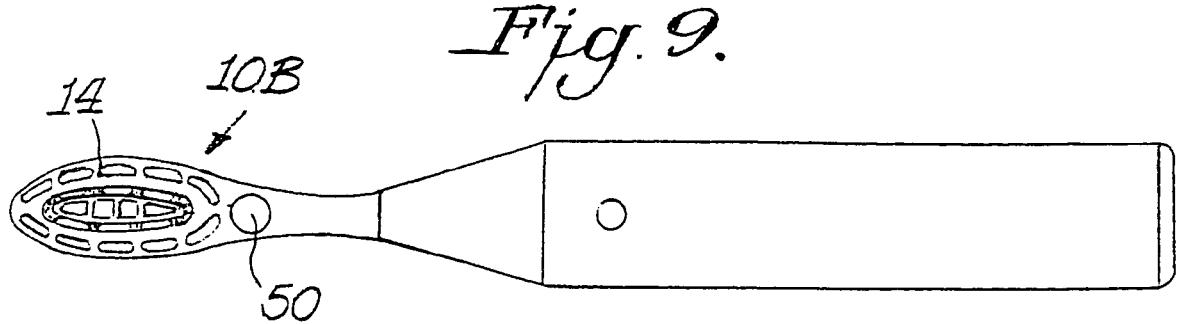
FIG. 9 is a top plan view of a powered toothbrush in accordance with this invention.

FIG. 9 illustrates a toothbrush 10B which includes a power driven movable disc or section 50 having cleaning elements. The movable section 50 could be oscillated rotationally such as by using the type of drive mechanism shown in U.S. Pat. No. 5,625,916, or could move in and out using the type of drive mechanism shown in U.S. Pat. No. Re35, 941; all of the details of both patents are incorporated herein by reference thereto. Alternatively, the other types of drives referred to above could move section 50 in other manners and directions. Although FIG. 9 shows movable section 50 to be at one end of the head, the movable section(s) could be located at any desired location on the head.

What is claimed is:

1. A toothbrush comprising a handle, a bead secured to the handle, the head having a movable portion and a fixed portion surrounding the movable portion, cleaning elements mounted in the fixed and movable portions, at least one cleaning element included in en area between the fixed and movable portions of the head, and a resilient membrane surrounding said movable portion, said resilient membrane extending between at least a portion of a peripheral surface of the fixed portion and at least a portion of a peripheral surface of said movable portion to connect said fixed and movable portions, said membrane being capable of flexing to alter its original orientation during use of said toothbrush and then recovering to assume its original orientation randomly during use of said toothbrush.

2. The toothbrush of claim 1 wherein said at least one additional cleaning element comprises bristles secured to the membrane by anchor free tufting.

3. The toothbrush of claim 1 wherein the at least one additional cleaning element comprises movable wipers.

4. The toothbrush of claim 3 wherein the movable wipers are mounted on the resilient membrane and rotate towards one another upon application of sufficient force on the toothbrush and away from each other upon release of that force.

5. The toothbrush of claim 1 wherein said movable portion is an island, and said membrane completely surrounding said island to resiliently join said island to said fixed portion.

6. The toothbrush of claim 5 wherein said fixed portion is an open frame made of generally rigid material, and said island including a rigid perimeter.

7. The toothbrush of claim 6 wherein said open frame is generally oval shaped having an oval shaped central opening in which said island is centrally located.

8. The toothbrush of claim 7 wherein said island includes rigid bridge members extending across said perimeter to separate said cleaning elements mounted in said island into spaced sets of cleaning elements.

9. The toothbrush of claim 6 wherein said island moves in and out generally perpendicular to said frame in response to pressure applied to said cleaning elements during use of said toothbrush.

10. The toothbrush of claim 1 wherein said fixed portion is a generally open frame made of rigid material, said movable portion being an Island made of a rigid material which is the same material as said fixed portion, said island including a perimeter.

11. The toothbrush of claim 10 including aligned straps on each side of said perimeter and integral with said perimeter and with said frame to connect said perimeter and said frame together.

12. The toothbrush of claim 11 wherein said straps comprise a pivot axis for permitting said island to rock in clockwise and counterclockwise directions about said straps.

13. The toothbrush of claim 12 wherein said straps are transversely centrally located with respect to a longitudinal axis of said island.

14. The toothbrush of claim 13 wherein said membrane fills the open space between said island and said frame.

15. The toothbrush of claim 14 wherein said membrane extends completely around said island including under said straps.

16. The toothbrush of claim 14 wherein said membrane comprises two U-shaped portions extending up to and terminating at said straps.

17. The toothbrush of claim 12 including wipers mounted on said membrane on each side of said straps.

18. The toothbrush of claim 17 wherein said wipers move in accordance with the rocking movement of said island whereby when said island is moved in a counterclockwise direction said wipers which are located on one side of said straps are tilted toward said straps with said wipers on the other side of said straps being tilted away from said straps and when said island is moved in a clockwise direction-said wipers are oppositely tilted to result in simultaneously opening and closing motions of said wipers during the rocking of said island.

19. The toothbrush of claim 1 wherein said cleaning elements include at least one prophy cup.

20. A toothbrush comprising a handle, a head secured to the handle, the head having a movable portion and a fixed portion surrounding the movable portion, cleaning elements mounted in the fixed and movable portions, a resilient membrane extending between at least a portion of the area between the fixed and movable portions and the membrane being capable of flexing to alter its original orientation during use of said toothbrush and then recovering to assume its original orientation randomly during use of said toothbrush, and wherein at least one additional cleaning element is included in an area between the fixed and movable portions of the head.

21. The toothbrush of claim 20 wherein the additional cleaning elements comprise movable wipers.

22. The toothbrush of claim 21 wherein the movable wipers are mounted on the resilient membrane and rotate towards one another upon application of sufficient force on the toothbrush and away from each other upon release of that force.

23. A toothbrush comprising a handle, a head secured to said handle, said head having a movable portion including cleaning elements, a fixed portion surrounding the movable portion, at least one additional cleaning element is included in an area between the fixed and movable portions of the head, a resilient membrane extending between at least a portion of said fixed portion and at least a portion of said movable portion, and support members connecting said fixed portion and said movable portion, a plurality of said support members each having a longitudinal axis extending transverse to the longitudinal axis of said head, wherein said movable portion is capable of pivoting about said transversely extending support members during use of said toothbrush.

24. The toothbrush of claim 23 wherein the at least one additional cleaning element comprises movable wipers.

25. The toothbrush of claim 24 wherein the movable wipers are mounted on the resilient membrane and rotate towards one another upon application of sufficient force on the toothbrush and away from each other upon release of that force.

26. The toothbrush of claim 23 wherein said movable portion is an island, and said membrane completely surrounding said island to resiliently join said island to said fixed portion.

27. The toothbrush of claim 26 wherein said island moves in and out generally perpendicular to said frame in response to pressure applied to said cleaning elements during use of said toothbrush.

28. The toothbrush of claim 23 wherein said fixed portion is a generally open frame made of rigid material, said movable portion being an island made of a rigid material which is the same material as said fixed portion.

* * * * *